US00PP09365P

United States Patent [19]

Zerr

[11] Patent Number: Plant 9,365

[45] Date of Patent: Nov. 7, 1995

[54] POINSETTIA PLANT NAMED 'FISSON'

[75] Inventor: Katharina Zerr, Simmern, Germany

[73] Assignee: Floris AG, Benningen, Switzerland

[21] Appl. No.: 327,930

[22] Filed: Oct. 24, 1994

[30] Foreign Application Priority Data

Feb. 9, 1994 [DE] Germany ..... EUP 155

[51] Int. Cl.[6] ..... A01H 5/00

[52] U.S. Cl. ..... Plt./86.4

[58] Field of Search ..... Plt./86.4

[56] References Cited

U.S. PATENT DOCUMENTS

P.P. 6,694 3/1989 Ecke ..... Plt./86.4

P.P. 8,259 6/1993 Jacobsen ..... Plt./86.4

*Primary Examiner*—James R. Feyrer

*Attorney, Agent, or Firm*—Foley & Lardner

[57] ABSTRACT

A distinct cultivar of poinsettia plant named Fisson, characterized by the combined traits of bright red bract color, broad elliptic bracts with pointed lobes, medium tall but comparatively narrow plant habit with good branching, dark green foliage, and medium early flowering response.

1 Drawing Sheet

The present invention relates to a new and distinct cultivar of poinsettia plant, botanically known as *Euphorbia pulcherrima,* and referred to by the cultivar name Fisson.

The new cultivar is a product of a planned breeding program carried out by the inventor Katharina Zerr in Hillscheid, Germany. The general objective of the breeding program was to create new cultivars having red bract coloration, dark green foliage, and good branching ability.

The new cultivar was originated from a hybridization made by the inventor in Hillscheid, Germany in 1992. The female parent was a proprietary hybrid seedling from unknown parentage and characterized by its bright red bract color and medium green foliage. The male parent was the cultivar Red Sails, an unpatented but commercial cultivar characterized by its strongly lobed red bracts and dark green foliage.

Seeds from the cross germinated in November 1992, and in January 1993 a cutting was taken by the inventor from each seedling. The plants grown from these cuttings started flowering after short day treatment in May 1993, and Fisson (Seedling No. 265) was selected from among these single stem plants.

Following final selection, additional cuttings were taken by the inventor in Hillscheid, Germany from the original seedling No. 265 and these cuttings were grafted on rootstocks of the cultivar Peterstar to introduce better branching ability. Peterstar, disclosed in U.S. Plant Pat. No. 8,259; is characterized by its bright red bract color, medium green foliage, comparatively compact plant habit, medium early flower response in autumn, and good branching ability.

The grafted plants were grown out and asexually propagated by or under the supervision of the inventor in Hillscheid, Germany by taking leaf cuttings from the scion, for the purpose of building up mother stock and confirming the stability of the new cultivar. Horticultural examination initiated in autumn 1993 and continuing thereafter has demonstrated that the combination of characteristics as herein disclosed for Fission are firmly fixed and are retained through successive generations of asexual reproduction. The new cultivar has the excellent branching characteristics of Peterstar while retaining all other desirable characteristics of seedling No. 265.

The following traits have been repeatedly observed and are determined to be basic characteristics of Fisson which in combination distinguish this poinsettia as a new and distinct cultivar:

1. Bright red flower color.
2. Broad-elliptical bracts with pointed lobes.

3. Medium tall, but comparatively narrow plant habit with good branching.
4. Dark green foliage. 5. Medium early flowering response.

Fisson has not been observed under all possible environmental conditions. The phenotype may vary significantly with variations in environment such as temperature, light intensity, and daylength without, however, any variance in genotype. The following observations, measurements and comparisons describe plants grown in Hillscheid, Germany, under greenhouse conditions which approximate those generally used in commerical practice.

Of the many commerical cultivars known to the inventor, the most similar in comparison to Fisson is the cultivar Lilo, disclosed in U.S. Plant Pat. No. 6,694. In general comparison to Lilo, Fisson has a lighter bright red flower color, similar dark green foliage, but broader plant habit and better branching ability. The flower response of Fisson is later, but bracts are already colored before cyathias mature. As a result, plants of Fisson are saleable at about the time as Lilo, but stay marketable for a longer time because cyathias hold very well and do not easily drop.

The accompanying color photographic drawing shows typical inflorescence and foliage of Fisson, with colors being as true as possible with illustrations of this type. In the photograph, a typical mature potted plant of Fisson appears on the left and a mature potted plant of comparison cultivar Lilo appears on the right.

In the following description, color references are made to The Royal Horticultural Society Colour Chart. The color values were determined indoors in a north light. The plants described were grown in Hillscheid, Germany (latitude 50° N). They were planted as rooted cuttings into 14 cm pots in early August, pinched in mid-August, and grown in the greenhouse under natural light conditions in late summer and autumn at 18° C. night temperature and 18° to 24° C. day temperature. Observations and measurements were taken at the beginning of flowering when 3 cyathias were open.

Classification:

*Botanical.*—*Euphorbia pulcherrima.*

*Commerical.*—Poinsettia, cv. Fisson.

Parentage:

*Male parent.*—Red Sails.

*Female parent.*—A hybrid seedling from unknown parentage, having bright red bracts and medium green foliage. The resulting seedling No. 265 was grafted to the cultivar Peterstar to improve branching ability.

Plant description:

*Form.*—Bushy, comparatively narrow, 8–9 branches.

*Growth habit.*—Medium height: 45–50 cm.

*Rooting.*—Medium: 20–24 days.

*Blooming season.*—From late November (about 9 weeks of response time).

*Blooming habit.*—Saleable in mid-November, when 3–6 bracts are colored approximately 1–2 weeks before cyathias open.

*Foliage.*—Size: Leaf is approximately 14 cm in length; petiole is 7 cm in length. Internodes: 30 mm. Color: New Foliage: Upper surface, medium to dark grren, 137A; under surface 137C. Old Foliage: Upper surface, dark green 139A; under surface 137B. Leaf Petiole: Dark red. Shape: Triangular with comparatively strong lobes, base somewhat wedge shaped. Texture: Upper side, smooth; lower side, weak veins. Edge of margin: Entire. Disease resistance: No specific diseases have been observed.

Flowering description:

*Cyathias.*—Borne: In a narrow cluster; may later grow somewhat apart. Quantity: 15–18. Retention: Good.

*Bracts.*—Mature bracts are elliptical, with lobes and pointed tips; younger bracts are ovate, sometimes a little concave; largest colored bract with petiole is 18 cm long.

*Color.*—Bright to dark red 45B.

*Aspect.*—Bracts face somewhat upright.

Reproductive organs:

*Glands, nectar cups.*—Yellow.

*Stamens.*—Dark red filament.

*Pollen.*—Plentiful, yellow in color.

*Styles.*—Dark red, 6-lobed stigma.

*Ovaries.*—Triangular, 3-celled, 3 ovules.

I claim:

1. A new and distinct poinsettia plant named Fisson, as illustrated and described.

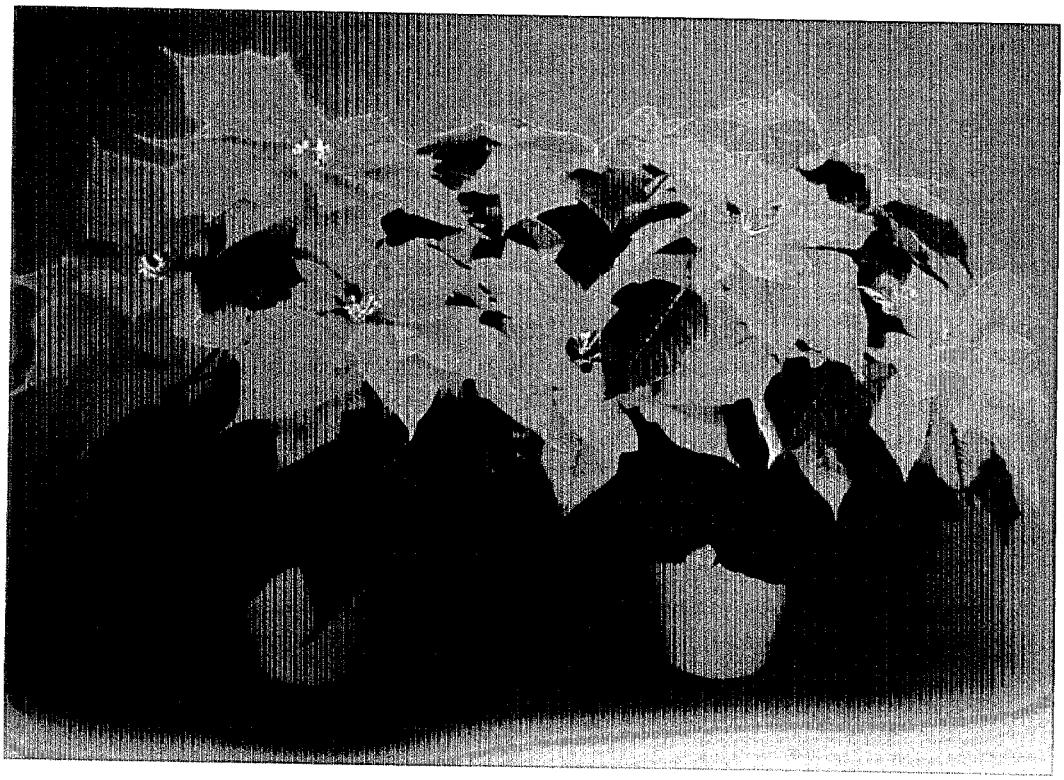

* * * * *